US007004912B2

(12) United States Patent
Polat

(10) Patent No.: US 7,004,912 B2
(45) Date of Patent: Feb. 28, 2006

(54) SYSTEMS AND METHODS FOR IMPROVING VISUAL PERCEPTION

(75) Inventor: Uri Polat, Gadera (IL)

(73) Assignee: NeuroVision, Inc., Singapore (SG)

( * ) Notice: Subject to any disclaimer, the term of this patent is extended or adjusted under 35 U.S.C. 154(b) by 101 days.

(21) Appl. No.: 10/169,609

(22) PCT Filed: Dec. 26, 2000

(86) PCT No.: PCT/IB00/02052

§ 371 (c)(1),
(2), (4) Date: Nov. 13, 2002

(87) PCT Pub. No.: WO01/47463

PCT Pub. Date: Jul. 5, 2001

(65) Prior Publication Data

US 2003/0109800 A1  Jun. 12, 2003

(30) Foreign Application Priority Data

Dec. 27, 1999 (IL) ........................ 133758

(51) Int. Cl.
  A61B 13/00  (2006.01)
(52) U.S. Cl. .................................... 600/558
(58) Field of Classification Search ................ 600/558, 600/300; 351/223, 237, 239
  See application file for complete search history.

(56) References Cited

U.S. PATENT DOCUMENTS

| 4,365,873 | A | 12/1982 | Ginsburg |
| 5,176,147 | A | 1/1993 | Bodis-Wollner |
| 5,206,671 | A | 4/1993 | Eydelman et al. |
| 5,262,632 | A | 11/1993 | Camp, Jr. |
| 5,589,897 | A | 12/1996 | Sinclair et al. |
| 5,694,199 | A | 12/1997 | Rodriguez |
| 5,956,126 | A | 9/1999 | Cody |

FOREIGN PATENT DOCUMENTS

| EP | 0 411 821 A | 2/1991 |
| EP | 0 544 631 A | 6/1993 |
| WO | WO 00 77760 A | 12/2000 |

OTHER PUBLICATIONS

Polat, Uri and Sagi, Dov, "Plasticity of Spatial Interactions in Early Vision" Department of Neurobiology, Brain Research, The Weizmann Institute of Science, Rehovot 76100, Israel.

Polat, Uri and Sagi, Dov, "The Architecture of Perceptual Spatial Interactions", Vision Res., vol. 34, No. 1, pp 73-78, 1994.

(Continued)

Primary Examiner—Max F. Hindenburg
Assistant Examiner—Brian Szmal

(57) ABSTRACT

In one embodiment, a system generates a succession of selected visual perception task images for presentation to a person, and receives respective inputs from the person based on the person's perception of each image, wherein subsequently generated images are based at least in part on the person's perception of one or more previously presented images. The generation and modification of images based on the person's input is repeated until at least one characteristic of the person's visual perception capabilities is adequately evaluated, improved to a desired level, or both.

22 Claims, 13 Drawing Sheets

OTHER PUBLICATIONS

Polat, Uri and Sagi, Dov, "Spatial Interactions in Human Vision: from near to far via experience-dependent cascades of connections", Proc. Natl. Acad. Sci. USA, Neurobiology, vol. 91, pp 1206-1209, Feb. 1994.

Levi, Dennis and Polat, Uri "Neural Plasticity in Adults with Amblyopia", Proc. Natl. Acad. Sci. USA, Neurobiology, vol. 93, pp 6830-6834, Feb. 1996.

Polat, Uri, Sagi, Dov and Norcia, Anthony "Abnormal Long-range Spatial Interactions in Amblyopia" Vision Res., vol. 37, No. 6, pp 737-744, 1997.

Levi, Dennis, Polat, Uri and Hu, Ying-Sheng, "Improvement in Venier Acuity in Adults with Amblyopia", Investigative Ophthalmology & Visual Science, Lippincott-Raven Publishers, USA, vol. 38, No. 8, Jul. 1997.

Levi, Dennis and Sharma, Vineeta, "Rapid Communication, Integration of Local Orientation in Strabismic Amblyopia", Vision Res. vol. 38, No. 6, pp 775-781, 1998.

Polat, Uri, "Functional Architecture of Long-range Perceptual Interactions" Spatial Vision, vol. 12, No. 2, pp 143-162, 1999.

FIGURE 3

SYSTEMS AND METHODS FOR IMPROVING VISUAL PERCEPTION

FIELD OF THE INVENTION

The invention relates generally to the field of vision improvement and, more specifically, to identifying and improving visual perception and acuity abilities, and improving the visual perception process and neural performance of a person over a communication network.

BACKGROUND INFORMATION

Human eyesight is a product of two separate processes that work together to form images for a person to "see." One of these processes, herein referred to as the physical component, concerns the physical structure of the various elements of the eye and how incoming light is manipulated and processed by the eye. Defects in the shape of the cornea, the retinal wall, or the optic nerve can impair or destroy the functionality of a person's eye and thus impair or eliminate the ability to perceive images. Fortunately, defects in the cornea of a person can be corrected through the use of glasses, contacts, or surgery such as laser keratotomy. Likewise, defects in the retina of a person are often repairable by surgery.

The second process involved in allowing humans to see images is herein referred to as the neurological component. This component concerns neural processing in the brain and how the brain analyzes information sent from the eyes to produce an image. A person can likewise have a number of defects in this component of the visual process, such as reduced visual acuity, reduced sensitivity for spatial contrast, reduced vernier acuity, spatial distortion, abnormal spatial interactions and impaired contour detection.

The physical component and the neurological component work together to form images that a person sees, or more precisely, that a person perceives. The term "perceives" is preferred because, although the physical component may capture certain details, defects in the neurological component may distort and destroy these details, therefore, the image that is "seen" by the person may not be exactly what is captured by the eyes. Consequently, the image that is perceived may differ in detail from the image that is seen by the eyes. Thus, the overall process of human eyesight is herein referred to as the visual perception process.

Defects in the neurological component of a person's visual perception process cannot be remedied through the use of corrective lenses or surgery. Therefore, alternate techniques must be employed to alleviate or correct visual defects in the neurological component of a person's visual perception process.

For example, a common defect in the neurological component of the visual perception process is a condition known as amblyopia. This is a perception defect where the brain incorrectly interprets and processes visual information it receives from the eyes, despite the fact that the physical structure of the eyes may be unimpaired. When addressing amblyopia in children, one approach to correcting defects in the neurological component is to occlude the non-amblyopic, dominant eye and "force" the brain to make greater use of the amblyopic eye. This approach generally strengthens the amblyopic eye and increases its visual acuity. But a significant shortcoming of this approach is that this method is typically only useful in children under the age of nine, and beyond that age the method generally provides insignificant results. Furthermore, occlusion of the non-amblyopic eye is accomplished through the use of an unsightly eye patch, and this often results in social and emotional problems for children. The eye patch may cause skin irritation, as well.

Amblyopic observers suffer from many or all of the neurological defects mentioned above, such as reduced visual acuity, reduced sensitivity for spatial contrast, reduced vernier acuity, spatial distortion, abnormal spatial interactions and impaired contour detection. Amblyopes may also have abnormally high degrees of intrinsic noise, which may form the basis of their abnormal contrast sensitivity function.

SUMMARY OF THE INVENTION

Systems and methods for evaluating, quantifying and improving a person's visual perception capabilities are provided.

In one embodiment, a system generates a succession of selected visual perception task images for presentation to a person, and receives respective inputs from the person based on the person's perception of each image, wherein subsequently generated images are based at least in part on the person's perception of one or more previously presented images. The generation and modification of images based on the person's input is repeated until at least one characteristic of the person's visual perception capabilities is adequately evaluated, improved to a desired level, or both.

Other and further aspects and advantages of the invention will become apparent from the following detailed description and accompanying drawings.

BRIEF DESCRIPTION OF THE DRAWINGS

In the figures of the accompanying drawings, like reference numbers correspond to like elements, in which:

FIG. 3 illustrates further embodiments of Visual Perception Task Images.

DETAILED DESCRIPTION OF THE PREFERRED EMBODIMENTS

Terminology

As used herein, the term "Visual Perception Task Image" or "VPT Image" refers to an image generated for use in testing, treating, or improving a person's visual perception process.

As used herein, the term "Visual Perception Task" or "VPT" refers to a visual perception test or task employing one or more VPT images in order to measure or improve a person's visual perception process.

As used herein, the term "Visual Perception Task Session" or "VPT Session" refers to a plurality of VPTs that are presented to a person to test or improve their visual perception process. Each VPT Session is generally designed to target a specific aspect of the visual perception process.

Visual Perception Task Images

Figure 1:
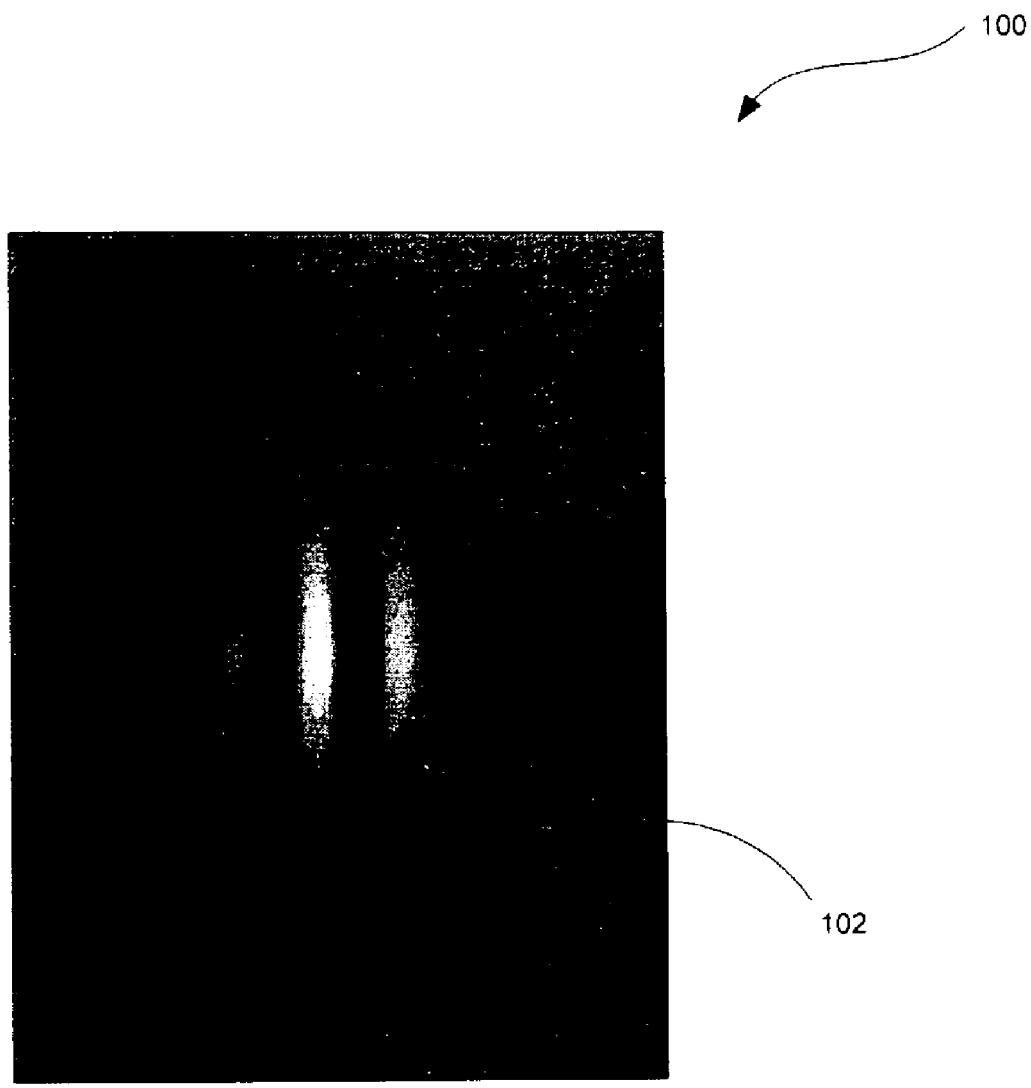
FIG. 1 illustrates one embodiment of a Visual Perception Task Image.

Beginning with FIG. 1, an exemplary Visual Perception Task Image (VPT Image) is shown. The VPT Image 100 of FIG. 1 comprises a single target Gabor patch 102 designed to activate neurons in the visual cortex. It should be noted that the VPT Image 100 can take the form of any visual stimulus, and is not limited to Gabor patches.

The Gabor patch 102 is a luminance pattern defined by a collection of odd (sine) and even (cosine) wave functions with limited spatial extent (and/or temporal extent). These functions are referred to as Gabor functions. The Gabor functions include variables that describe the pattern orientation, wavelength (width of a single black-white cycle) and spread of the Gaussian envelope.

Gabor functions are significant because they have been shown to efficiently describe the shape of receptive fields in the mammalian visual system. Neurons in the primary visual cortex receive retinal inputs with weights distributed over space in a shape that fits the Gabor function. In humans, it has been shown that visual pattern detection is performed by multiple localized filters, each covering a range of retinal space, orientations and wavelengths. The filters weigh visual input by a function that fits the Gabor function, each filter having its own parameter set (location, orientation, wavelength). These detectors underlie both pattern detection and segmentation.

Figure 2:
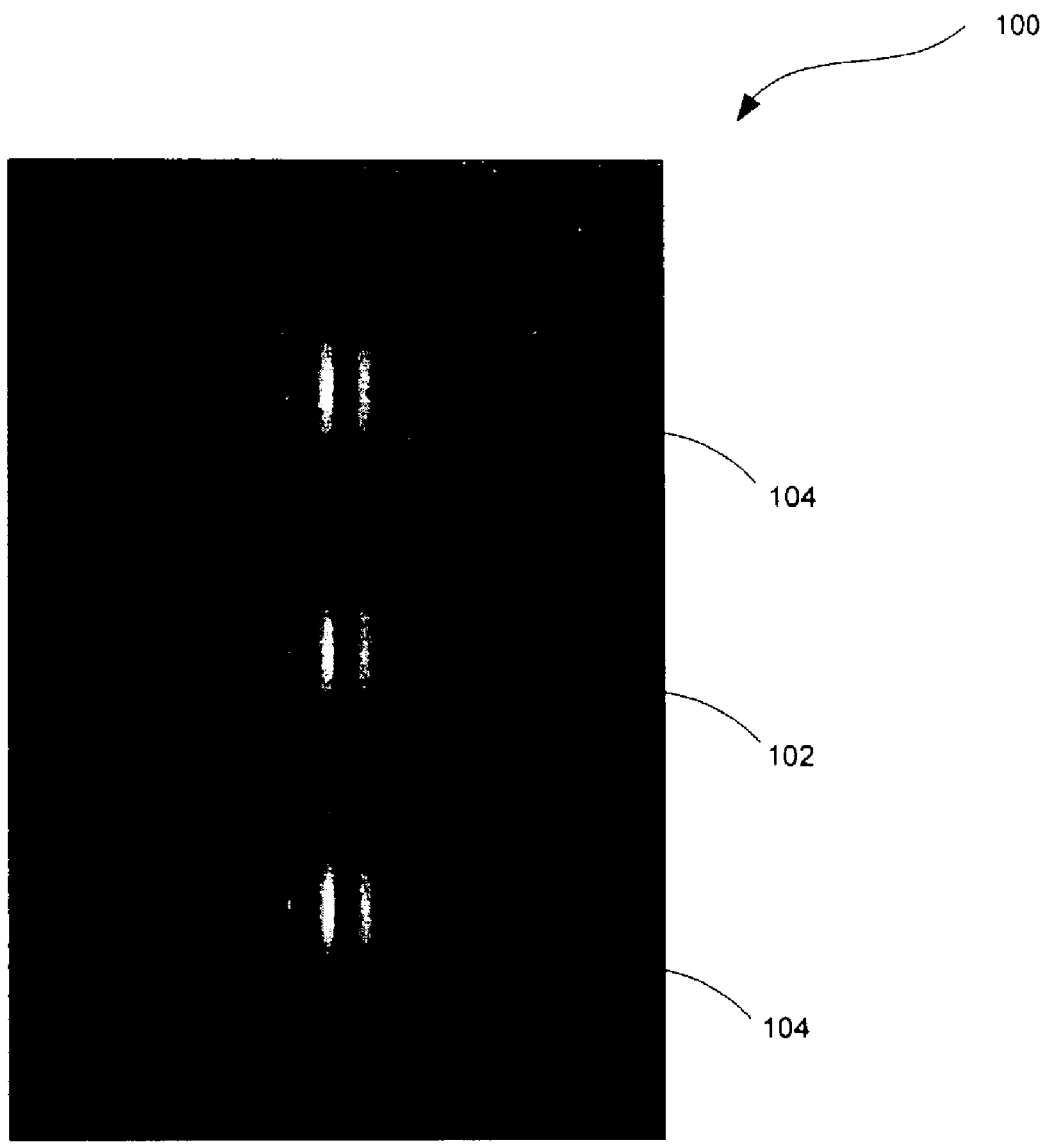
FIG. 2 illustrates a second embodiment of a Visual Perception Task Image.

Another VPT Image 100 is illustrated in FIG. 2, this time comprising a central target Gabor patch 102 flanked by two more Gabor patches 104 of similar orientation and spatial frequency placed laterally of the central Gabor patch. In this embodiment, the target Gabor patch 102 preferably coincides with a fixation point of an observer (the target patch 102 being fovean) sitting a distance of about 0.5–2.5 meters from a display screen presenting the VPT image. The Gaussian envelope size ($\sigma=\lambda=0.15°$) may be such that at least one cycle is within a range of $\pm\sigma$ from the Gaussian center. The carrier spatial frequency of the Gabor patches may be 6.6 cycles per degree ($\lambda=0.15°$) and mask contrast may be 40%. The distance d between the target Gabor patch 102 and the flanking patches 104 may be $1.5\lambda$. The initial contrasts of the patches may be in the range of 8–50%, for example. In short, each visual image is characterized by a parameter comprising at least one of a contrast, a spatial frequency, a distance between the images, a local and global orientation, presentation time, and possibly other parameters as well.

It should be noted that the invention contemplates use of a number of alternative embodiments of the VPT Images 100. This is because many visual perception deficiencies exist, and each deficiency generally requires a different set of VPT Images 100 to best identify the particular deficiency and work to improve it. Therefore, the invention contemplates using a large number of different VPT Images 100 to identify and improve many different types of visual perception deficiencies. These different VPT Images 100 use changes in parameters such as contrast, contours, spatial frequency, distance between the images, local and/or global orientations of the images, and other attributes to develop improved neurological function. Because the VPT Images 100 are typically computer-generated images, they may also be either static or dynamic.

Furthermore, the VPT Images 100 are not restricted to Gabor patches, but rather any kind of visual image, including straight lines, curved lines, or other shapes. The particular VPT Image 100 used is selected based upon which neurological functions require improvement. Accordingly, the embodiments shown in FIGS. 1 and 2 are for purposes of illustration only, and are not meant as limitations on the invention.

Figure 3:
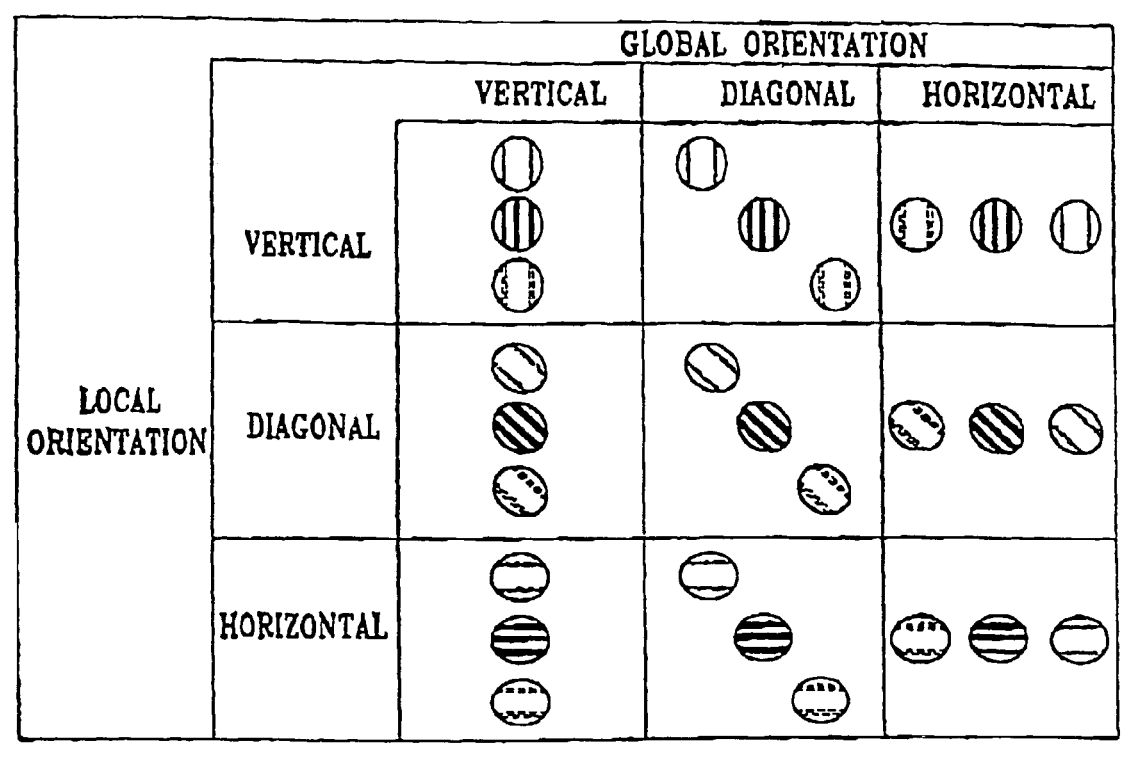

Variations of the VPT Images of FIGS. 1 and 2 may also be used. For example, another variation of the VPT Image 100 of FIG. 1 may consist of sequentially adding one or more flanking Gabor patches 104 that are similar in appearance to the target Gabor patch 102. And for the VPT Image 100 of FIG. 2, a variation may consist of rotating the local orientations of the Gabor patches 102 and 104, as well as their global orientation. Examples of alternate variations of the VPT Images are shown in FIG. 3.

Visual Perception Tasks

A Visual Perception Task (VPT) comprises one or more VPT Images 100 that are presented to a person in sequence, wherein at least one of the VPT Images 100 generally includes a target. As used herein, the term "target" refers to a specific portion of the VPT Image that the person is expected to focus on or detect, such as a Gabor patch or some other visual stimulus.

When two or more VPT Images 100 are used in a VPT, generally less than all of the VPT Images 100 used will contain the target. For example, if two VPT Images 100 are used, one VPT Image 100 will have a target that the person is expected to detect while the other VPT Image 100 will not. And when a VPT comprises only one VPT Image 100, the person is generally expected to detect some characteristic of the image, such as whether a target Gabor patch is offset from flanking Gabor patches, or whether a contour can be seen.

The one or more VPT Images 100 are shown to a person during the VPT, and the person is then asked to perform the VPT by identifying the target or the characteristic of the image. The VPTs vary, thus there may be a single static or dynamic VPT Image used in a VPT, or there may be two or more VPT Images displayed in sequence.

After the VPT is presented, the person is asked to provide a response (or "input") based upon his or her perception of the VPT Images 100. For example, the person can be asked to indicate whether he or she perceived the target, or whether the target has been offset from flankers. The person can provide this input through a variety of mechanisms, for instance by answering a yes/no question, a multiple choice question, a true/false question, a right/left question, or other similar questions.

The person provides the input using an input device such as a computer keyboard or mouse. Other input means, such as voice recognition, touch-screens, joysticks, trackballs, computer pens, or touch-pads can also be used. For some VPTs, such as those testing perception of contours, the input may not be a response to a question, but rather, the person may indicate a perceived contour formed by the images using a mouse to outline the contour.

One or more further VPTs are then generated and presented to the person based, at least in part, upon the person's response to the preceding VPT. Normally, if the person correctly performed the preceding VPT and detected what was expected, the further VPT can be configured to be more difficult. Or if the person was unable to perform the preceding VPT, the further VPT can be configured to be easier to perceive for the person. Alternately, and particularly when the level of difficulty is at or near the person's threshold, the further VPT can be designed to maintain the same level of difficulty. This taxes the person's visual perception process and further works the person at the thresholds of his or her visual perception abilities. These further VPTs are preferably generated until the person is no longer making progress in the particular treatment session.

More particularly, the further VPTs are generated by varying one or more parameters associated with the VPT Images 100. These parameters may include, but are not limited to, contrast, spatial frequency, distance between images, local and global orientation, and the duration of time an image is displayed. Combinations of parameters may be manipulated as well, such as contrast and exposure duration of the VPT Image 100. As explained in greater detail herein, these parameters are quantified and expressed in numerical terms to allow for analysis and manipulation using software containing functions and algorithms for this purpose.

The VPTs can be administered in different ways. Typically a person uses both eyes when performing the VPTs. However, the methods and systems of the invention can be used to build acuity in only one eye by blurring or covering the other eye. Then stereoscopic vision can be developed using both eyes. This technique is more adapted for use in adults. Further, especially in the case of children, entertaining content can be added to or built into the VPTs to keep their interest level high.

VPT Example 1

Figure 4A:
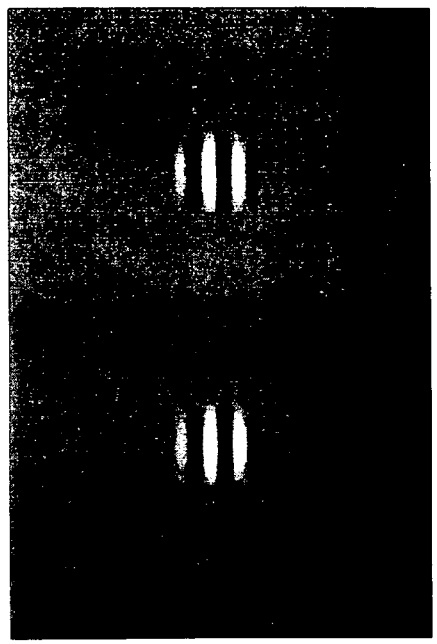
FIGS. 4A through 4D illustrate two embodiments of Visual Perception Tasks.
Figure 4B:
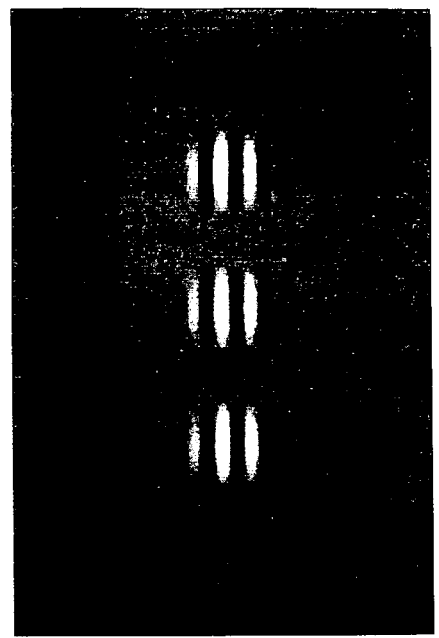

Turning now to FIGS. 4A and 4B, an example of a VPT is shown where a person's contrast sensitivity is addressed. In this example, the VPT comprises two VPT Images 100, one in FIG. 4A and the other in FIG. 4B. The VPT begins with a person focusing on a target area, which is generally the center of the display screen. Some form of marker may be displayed prior to the VPT Images 100 being shown to aid the person in focusing on the target area. Next, the two VPT Images 100 are shown to a person in sequence. The VPT Image 100 of FIG. 4A appears on screen for a short duration of time, then no image is shown for a short duration of time, and finally the VPT Image of FIG. 4B is shown for a short duration of time. One of the two images contains the "target" that the person is expected to perceive. Here, the target appears in the second image, which is FIG. 4B.

The person now provides an input to indicate which VPT Image 100 contained the target. Again, the appropriate user input in this example would be to acknowledge that the second image (FIG. 4B) contained the target. Once the person inputs a response, a further VPT is generated and presented to the person.

Figure 4C:
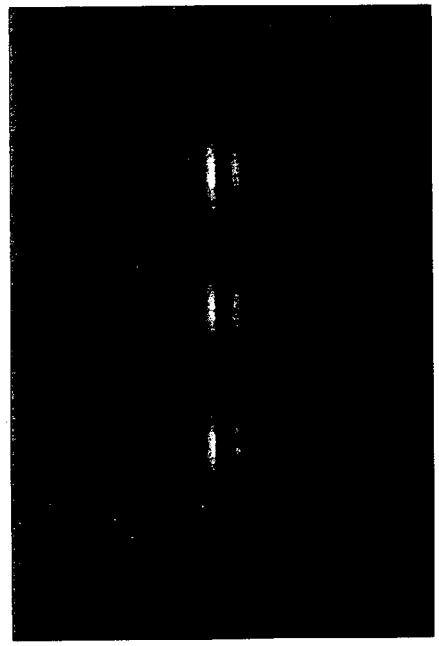
Figure 4D:
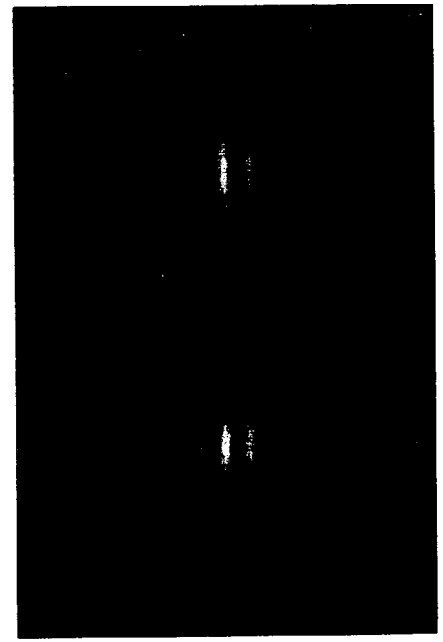

If the person has provided a correct response to the VPT of FIGS. 4A and 4B, the next successive VPT will preferably be slightly more difficult. By way of example, this may be accomplished by decreasing the contrast of the VPT Images 100. As shown in FIGS. 4C and 4D, the new VPT Images 100 have a lower contrast, thereby making the target more difficult to perceive. The VPT Images 100 of FIGS. 4C and 4D can then be presented as a VPT for the person to perform. This decreasing of contrast level then continues as the person successfully performs the VPTs until the person is no longer able to perceive the target.

The order of the VPT Images 100 is random, which is why the order of the VPT Images in FIGS. 4C and 4D varies from that of FIGS. 4A and 4B. And in the event the person provides an incorrect response, the contrast level can be increased to make the target easier to perceive.

Figure 4E:
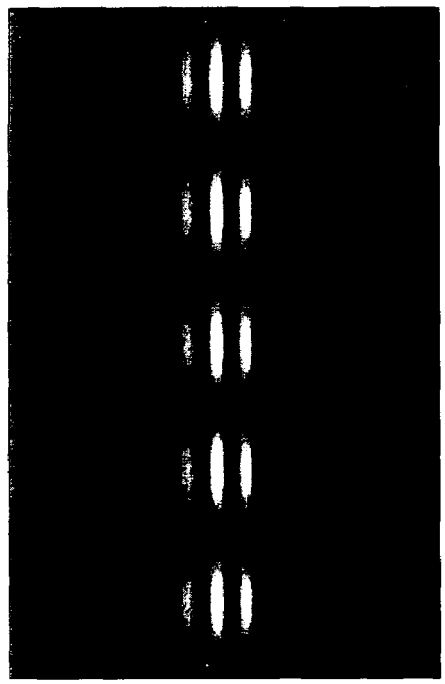
FIGS. 4E and 4F illustrate another embodiment of a Visual Perception Task.
Figure 4F:
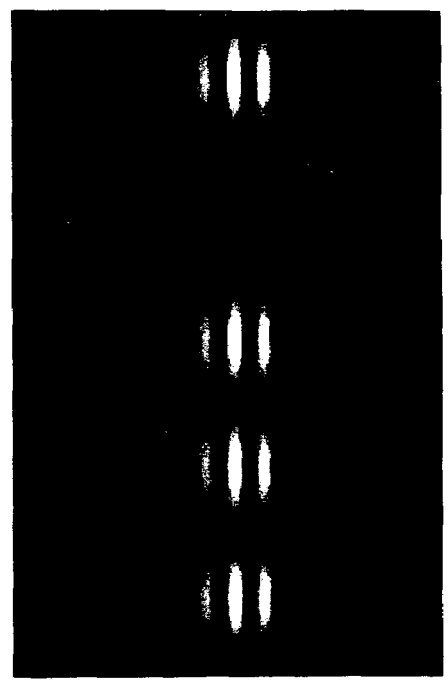

Many variations of the VPTs of FIGS. 4A through 4D are possible. For instance, the number of Gabor patches used in each VPT Image 100 can vary. A VPT may comprise two VPT Images 100, where one VPT Image 100 has a single Gabor patch and the other VPT Image 100 has no Gabor patches. Or, as shown in FIGS. 4E and 4F, the VPT can comprise two VPT Images 100 where one VPT Image 100 has four Gabor patches and the other VPT Image 100 has five Gabor patches. Any other number of Gabor patches can be used for this type of VPT, as long as one VPT Image 100 of the VPT has "x" patches, and the other VPT Image has "x−1" patches. This ensures that the VPT can be used to determine whether a person can detect a target Gabor patch. It should be noted that if the VPT is using a plurality of Gabor patches, the target Gabor patch can be any of the patches and does not necessarily have to be the center patch of the image.

VPT Example 2

Turning to FIGS. 5A through 5D, four more VPTs are shown that address vernier acuity. Here, each VPT comprises a single VPT Image 100 that contains three Gabor patches and is exposed to a person for a short duration of time. In each of these VPTs, the person is asked to indicate whether the central Gabor patch is offset to the left or right of the flanking Gabor patches.

Figure 5A:
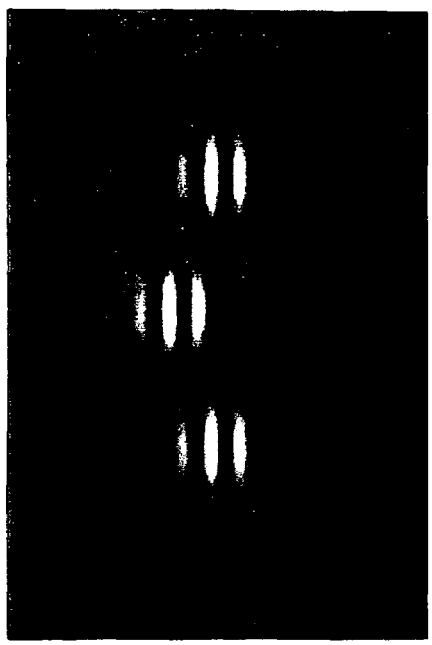
FIGS. 5A through 5D illustrate four more embodiments of Visual Perception Tasks.
Figure 5B:
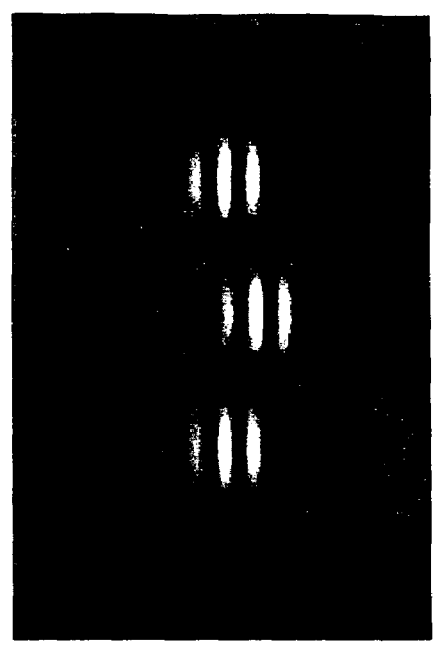
Figure 5C:
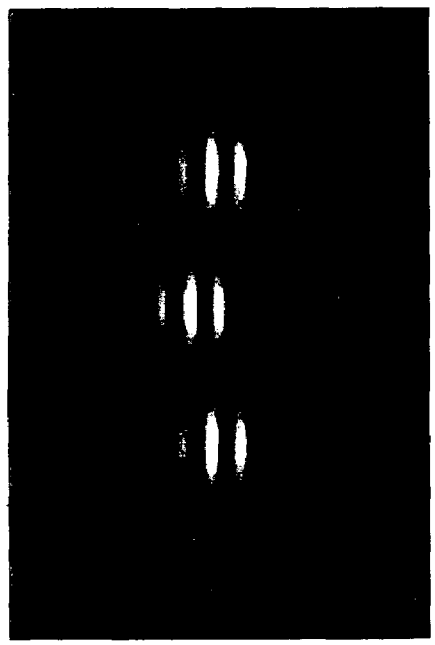
Figure 5D:

FIGS. 5A through 5D illustrate VPTs in descending order of difficulty, from greatest to least offset of the center Gabor patch. Therefore, FIG. 5A is the easiest VPT of the four, and FIG. 5D is the most difficult. As a person correctly performs the VPTs, the offset level will decrease towards what is shown in FIG. 5D and beyond until the person cannot detect an offset. And if the person incorrectly answers VPTs, the offset will head in the direction of FIG. 5A and beyond.

Variations of the VPTs of FIGS. 5A through 5D are also possible. For instance, the offset can occur in the top or bottom Gabor patch instead of the center Gabor patch. And in another variation, the three Gabor patches can be lined up diagonally or horizontally instead of vertically as is the case in FIGS. 5A through 5D.

VPT Example 3

Figure 6A:
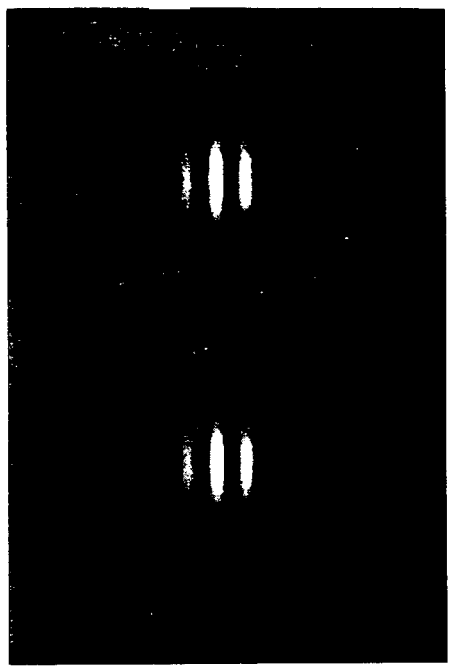
FIGS. 6A through 6D illustrate two more embodiments of Visual Perception Tasks.
Figure 6B:
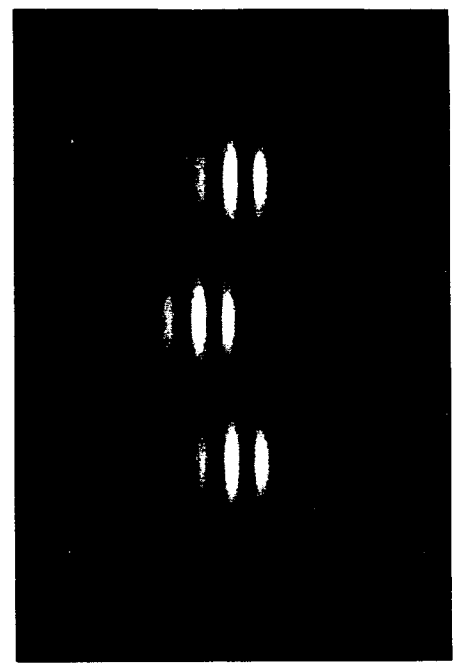
Figure 6C:
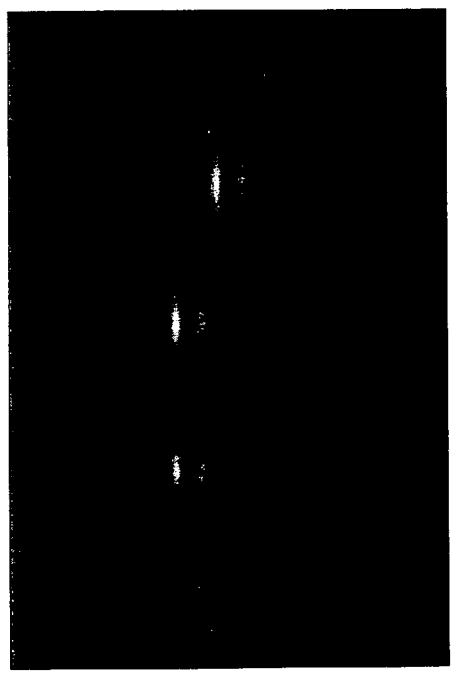

Turning now to FIGS. 6A through 6D, two more VPTs are illustrated (FIGS. 6A/6B are the first VPT, and FIGS. 6C/6D are the second VPT). Here, each VPT comprises two VPT Images 100 where one VPT Image has three Gabor patches and the other has two, similar to FIGS. 4A through 4D. The difference between these VPT Images and those of FIGS. 4A through 4D is that here, one of the Gabor patches is offset from the others. In FIGS. 6A and 63, the center Gabor patch is offset. And in FIGS. 6C and 6D, the top Gabor patch is offset.

The offsetting of one of the Gabor patches tends to change how a person perceives the image. This is because the flanking Gabor patches tend to either facilitate or suppress detection of the target Gabor patch. Whether they facilitate or suppress depends on a number of factors, including contrast level of the flankers, distance of the flankers from the target, and the person's visual abilities. Thus, offsetting one of the Gabor patches, as done here, creates VPTs that differ than those of FIGS. 4A through 4D.

Figure 6D:

In these VPTs, the person is again required to detect which VPT Image 100 has the target patch. In the VPT of FIGS. 6A and 6B, the center Gabor patch is the target. In the VPT of FIGS. 6C and 6D, the bottom Gabor patch is the target.

VPT Example 4

Figure 7A:
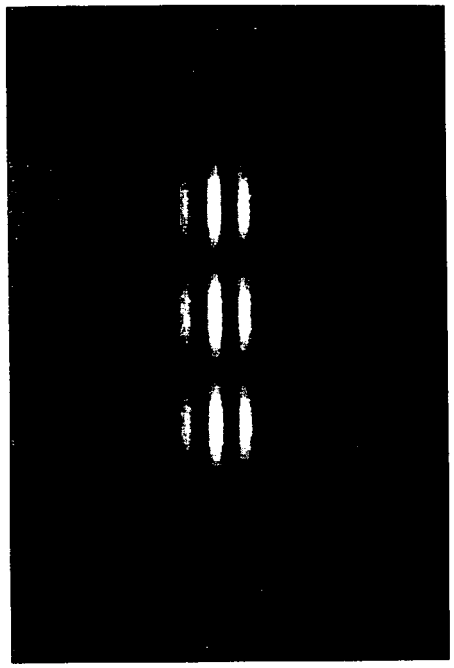
FIGS. 7A through 7D illustrate two more embodiments of Visual Perception Tasks.
Figure 7B:
Figure 7C:
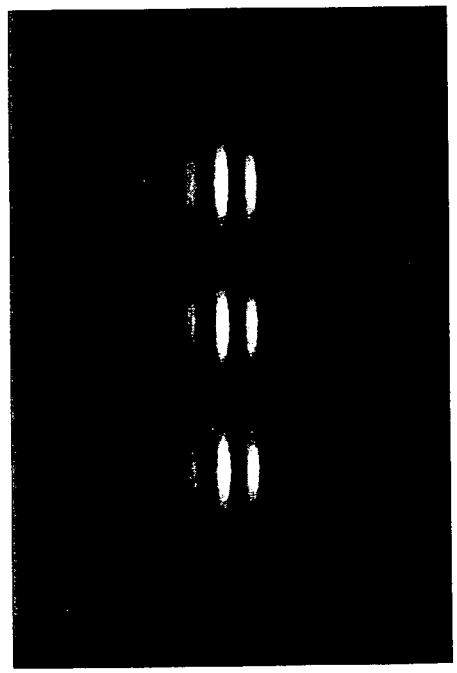
Figure 7D:
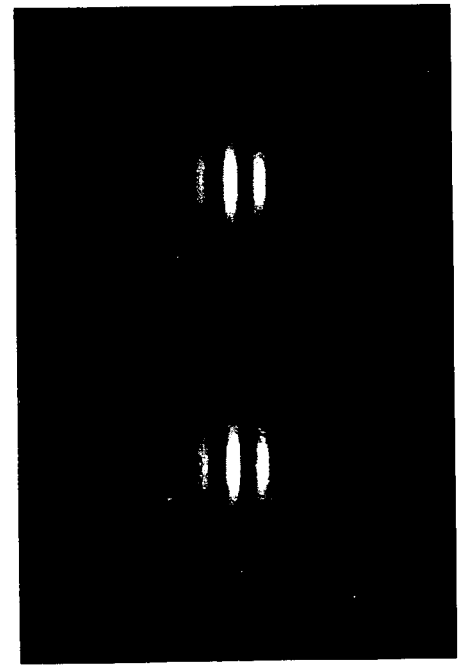

Turning now to FIGS. 7A through 7D, two VPTs of another type are shown that address contrast sensitivity and lateral interactions. Here the Gabor patches are always aligned, but parameters such as distance between the patches and contrast can be varied. Each VPT comprises two VPT Images 100 where again one VPT Image 100 has a target patch. To make the VPTs more difficult, either the contrast level is lowered, or the distance between the Gabor patches increased, or both. FIGS. 7C and 7D illustrate how the VPT Images 100 of FIGS. 7A and 7B are configured when the distance between patches is increased.

As explained in greater detail herein, as a person progresses through the VPT Session, the parameter being manipulated, whether it is contrast level or another parameter such as offset, will reach a value that is close to the person's threshold or visual limitation and will tend to stabilize around an average value. This value, referred to herein as the "stabilized value", can be used for many purposes, including to analyze the person's performance and to gauge whether the person is improving. This information is also used in configuring future VPTs for the person. Another useful value that is related to a VPT and used for analysis is a combination of the stabilized value and the VPT exposure duration. The VPT exposure duration refers to how long each VPT Image 100 was present on screen during the VPT.

For instance, in the VPT example of FIGS. 4A through 4D, assuming the person successfully performs the VPTs, the contrast of the Gabor patches will decrease until a stabilized value is reached. This stabilized value, here relating to the threshold contrast value where the person can still perceive the target, is used when evaluating a person's performance. Another useful data item related to this type of VPT is a combination of the stabilized value and the frame exposure duration.

In the VPT example of FIGS. 5A through 5D, if the person successfully performs the vernier acuity VPTs, the offset of the center Gabor patch will decrease until a stabilized value is reached, here relating to the threshold where the person can still detect an offset of one of the patches. Again, this stabilized value is used when evaluating a person's performance, and another useful data item here is a combination of the stabilized value and the frame exposure duration.

VPT Sessions

The administration of similar VPTs designed to target a specific aspect of the visual perception process is referred to as a VPT Session. For example, VPTs designed to improve a person's vernier acuity are referred to as a VPT Session for vernier acuity. Different VPT Sessions are designed to target all of the different aspects of the visual perception process, and preferred systems and methods utilize all of these different VPT Sessions. Generally, only one aspect of a person's visual perception process is targeted for improvement at a time, accordingly, one VPT Session is typically administered at each sitting. However, depending on time constraints, a single VPT Session can be administered over the course of two or more sittings.

Each VPT Session is made up of several series of VPTs. Although the VPTs contained in each series are very similar and address the same aspect of the person's visual perception process, each series has a slight variation from the others. For example, in the VPTs of FIGS. 4A through 4D, the variation in each series can be the distance between the center Gabor patch and the flanking Gabor patches. As these series of VPTs are administered, each series will generate its own stabilized value, and the stabilized values from each series are then used to evaluate the person.

Communication Network Architecture

Figure 8:
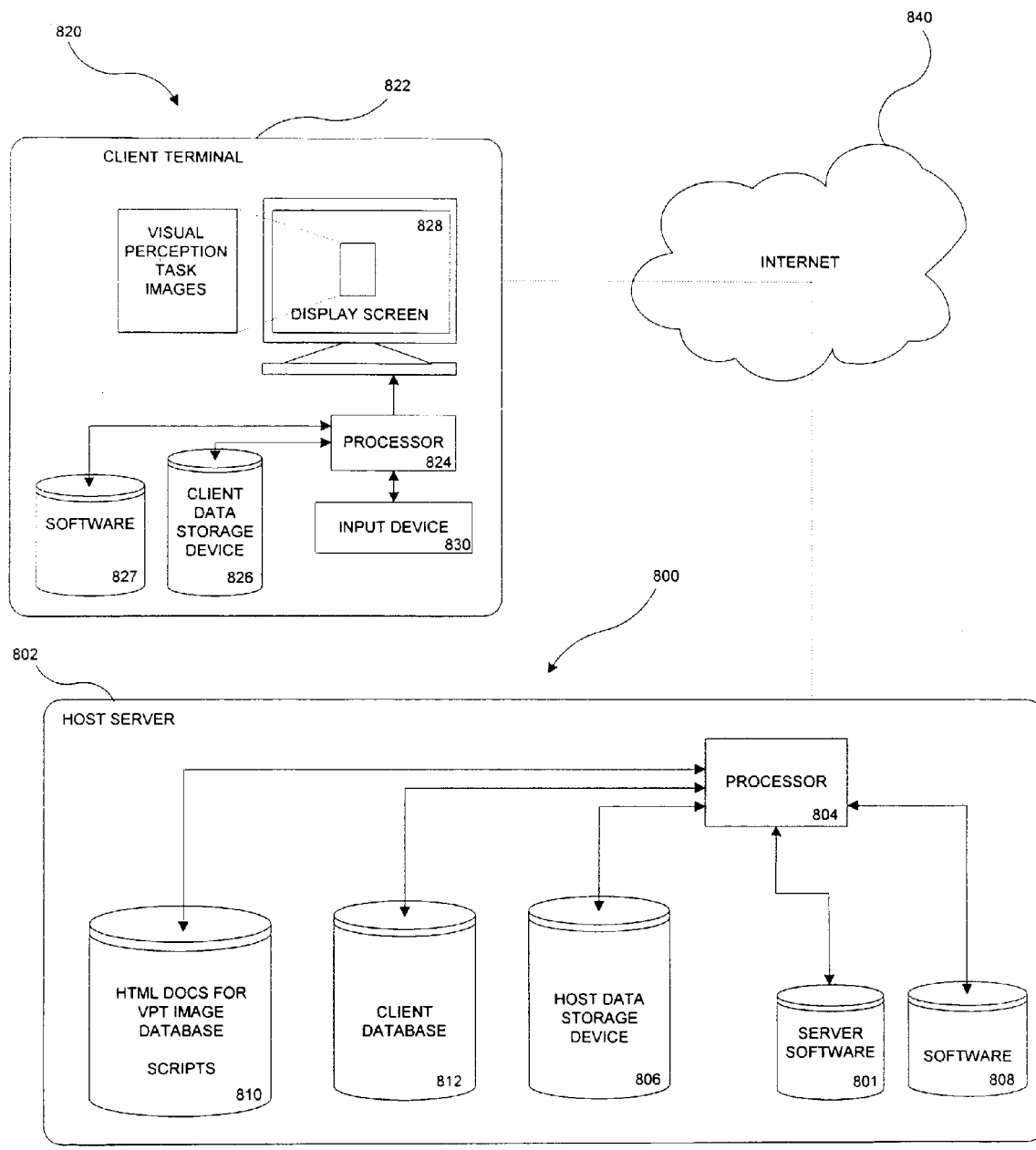
FIG. 8 is a simplified diagram of an internet-based system for identifying, quantifying and improving visual perception abilities of a person, in accordance with the invention.

Turning to FIG. 8, preferred implementations of the invention may be performed using a host server 800 and a client terminal 820. Host server 800 is a computer system 802 or device on a network with server software 801 configured to receive and answer requests for information. Typically, computer system 802 is also dedicated to storing data files and managing network resources, including network traffic. Computer system 802 or device generally includes a processor 804 and a data storage device 806, and is typically connected to a global communication network, such as the Internet 840.

Host server 800, through processor 804, has access to software 808 comprising sequences of instructions that cause processor 804 to perform a number of acts in accordance with the preferred methods described herein. In an alternative embodiment, host server 800 can also have access to a web page data storage device 810 that can store Hypertext MarkUp Language (HTML) documents defining web pages for communicating with persons, including HTML documents generated for the VPT Images 100. Web page data storage device 810 can also store computer program scripts to generate web pages using an Active Server Pages (ASP) specification or Common Gateway Interface (CGI) specification.

Host server 800 also has access to a client database 812 that stores information concerning persons of the system. This information can include identification information and data relating to a person's performance during past VPT Sessions. In alternate embodiments, client database 812 may reside outside host server 800, such as at client terminal 820.

Client terminal 820 is a remote terminal that provides an interface for a person to access host server 800. Client terminal 820 is typically a computer system 822 or device that is communicatively coupled to host server 800 by a communication network, such as the Internet 840. Computer system 822 generally includes a processor 824, a data storage device 826, a display screen 828, an input device 830, and software 827 that comprises sequences of instructions that cause processor 824 to perform a number of acts in accordance with the methods described herein. An exemplary computer system for use in either the host server 800 or client terminal 820 is described below with reference to FIG. 12.

Administering Visual Perception Tasks Over a Communication Network

Host Server-Side

Figure 9:
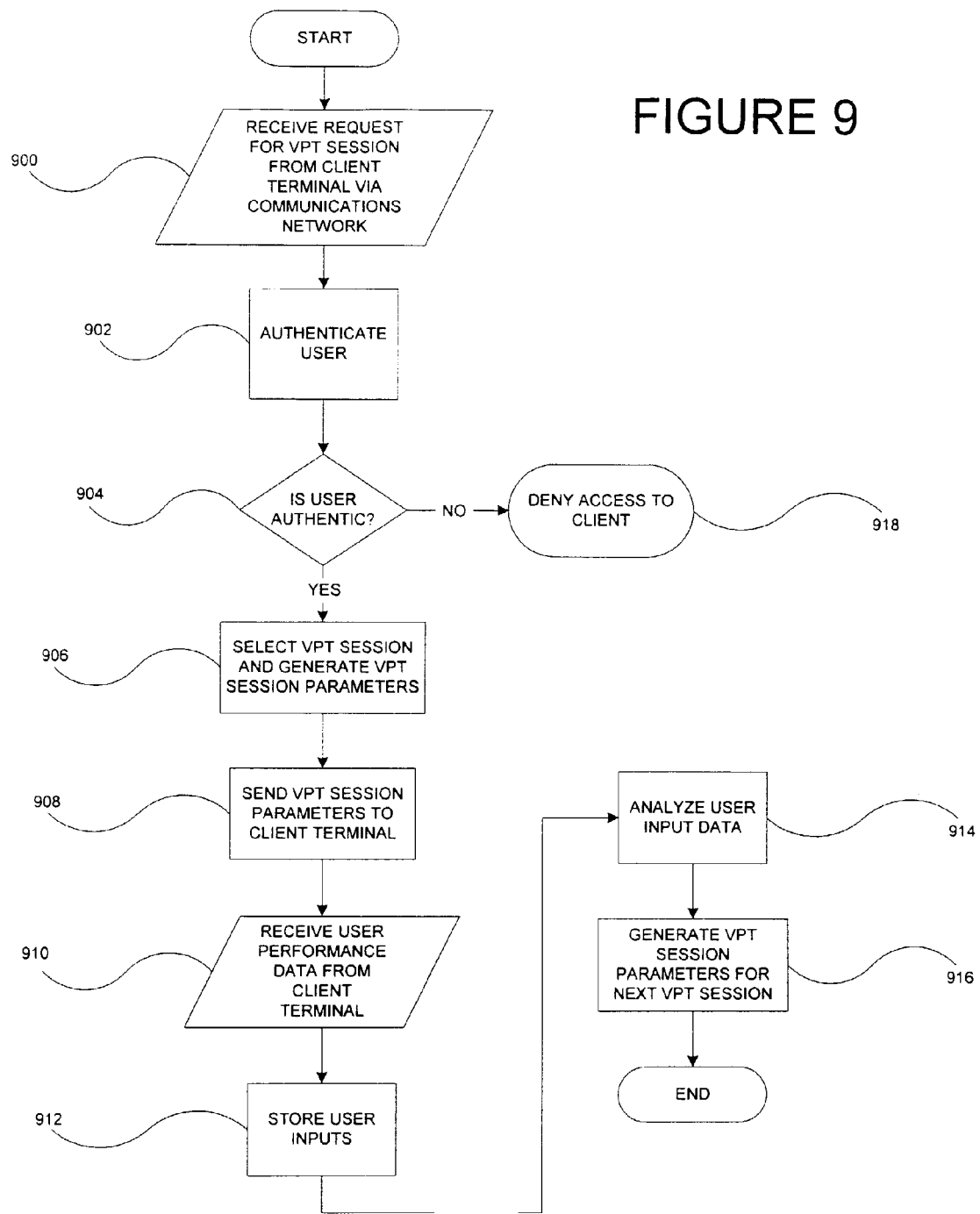
FIGS. 9 and 10 are flowcharts depicting methods for identifying, quantifying and improving visual perception abilities of a person from the perspective of a host server in the system of FIG. 8.

Turning to FIG. 9, a flowchart depicting a preferred implementation of a method of the invention is shown. The flowchart illustrates how the method is carried out at host server 800. Starting with step 900, host server 800 first receives a request from client terminal 820 for access to a VPT Session. This request is sent from client terminal 820 to host server 800 over a communication network, such as the Internet 840. For ease of reference, the Internet will be the communication network referenced. It should be noted, however, that many other types of communication networks may be utilized by the invention.

Host server 800 can make itself accessible for such a request from client terminal 820 by providing an Internet website. Persons can visit the Internet website using a web browser such as Netscape Navigator (available at www-.netscape.com) or Microsoft Internet Explorer (available at www.microsoft.com), or a specially developed web browser may be used to access the site. Persons can then directly request access to a VPT Session from host server 800.

In step 902, an authentication routine is performed to determine whether the request from client terminal 820 is valid. In other words, host server 800 determines whether the person that is trying to access a VPT Session is authorized to do so. Generally, host server 800 does this by sending a request over the Internet to client terminal 820 for a username and password. The data then received from client terminal 820 in response to the username and password request is typically transmitted to host server 800 over the Internet in an encrypted format, or using certificates, which prevents unauthorized persons from viewing the data.

Moving to step 904, upon receiving the username and password data from client terminal 820, host server 800 compares that data to username and password data stored in client database 812. If host server 800 determines that the person is authentic, the process continues at step 906. If the person is deemed to be non-authentic, a message is sent to client terminal 820 informing the person that access to the VPT Sessions is denied, as shown in step 918. At that point, the person can be allowed to re-enter his or her username and password information a number of times. Generally, the number of times the person is permitted to re-enter the username/password information is limited to prevent persons from trying to gain unauthorized access. After a predetermined number of failed authentication attempts, host server 800 will typically ignore further requests from client terminal 820 for a predetermined length of time.

In step 906, after host server 800 determines that the username and password supplied are genuine, a VPT Session is selected and an initial set of VPT Session parameters are generated. Typically, these parameters are defined in advance. The VPT Session is selected according to the methods described below with reference to FIG. 10, and the VPT Session parameters are generated as explained below with reference to step 916. The VPT Session parameters define items such as contrast level, contours, spatial frequency, distance between objects, target placement, local and/or global orientations, and presentation time for each of the VPTs and VPT Images 100 being used to test or improve the visual perception process of a person.

Moving to step 908, the initial VPT Session parameters are then delivered to client terminal 820 over the Internet 840. Software resident on client terminal 820 is configured to receive the VPT Session parameters and use them to dynamically generate VPT Images 100 and VPTs. The VPT Session parameters transmitted can be encrypted, or can use certificates, for security purposes so no person can intercept the data. Once the parameters are delivered, the VPT Session can be carried out solely at client terminal 820 without the need for further interaction with host server 800. This preferred configuration allows the VPT Session to be administered to the person without delay or interruption.

Alternatively, the VPT Session parameters can be sent as web pages in a format such as the Hyper-Text Markup Language (HTML) format. The web pages sent will generally be full screen pages, encompassing the entire viewable area of the display screen rather than appearing within a frame of a web browser.

In another alternative configuration, administration of the VPT Session can be carried out primarily by host server 800, thus requiring data to be transferred back and forth between host server 800 and client terminal 820 during the session itself.

Moving to step 910, after the VPT Session has been administered to the person, host server 800 receives a set of person performance data from client terminal 820. The person performance data is data relating to the person's performance, which primarily comprises the stabilized values generated for each series of VPTs administered during a VPT Session, and can also include some or all of the user inputs received by client terminal 820. The person performance data is generated by client terminal 820 and then sent back to host server 800 over the Internet 840. This data can also be encrypted to prevent unauthorized persons from viewing the data.

In step 912, host server 800 stores the person performance data it receives from client terminal 820. The person performance data is generally stored on a data storage device, such as client database 812. The data may alternatively be stored on data storage device 806. This alternative may be preferred when, for instance, the personal information and medical records of clients are to be kept on a relatively secured storage device that is separate from the storage device that is storing the collection of user inputs. The data storage device 806 is further described below with reference to FIG. 12.

Moving to step 914, the host server 800 next analyzes the person performance data to reveal any visual perception deficiencies, and to determine the level of performance of the person's visual perception process. Software 808 provides instructions and data for processor 804 to carry out this analysis. This is done by comparing the person performance data to data collected from persons with "normal vision," i.e., based on generally acceptable levels of performance for each of the different aspects of the visual perception process, which helps gauge the person's level of performance. The processor 804 performs this comparison, using data related to that of a "normal observer," which is stored in data storage device 806.

When the VPTs contain flanking Gabor patches, it is also determined if the flankers tended to suppress or facilitate detection of the target Gabor patch. In addition, it is preferred data such as the person's personal medical data and history, results of past VPT Sessions, and statistical data for the general population be considered in the analysis.

Moving to step 916, new VPT Session parameters are generated for use in the next VPT Session, based at least in part upon the person performance data that was received by host server 800, and based at least in part upon the analysis conducted upon the person performance data by processor 804. These new parameters again define specific VPT Images 100 and VPTs to further improve the person's visual perception ability based upon the person's level of performance.

Host server 800 uses software 808 to make these analyses and determinations. The software uses the person's performance data, and in particular the stabilized values generated for each series of VPTs in a given VPT Session. These stabilized values are then provided as input for one or more algorithms for generating new VPT Session parameters.

First, the algorithm(s) use the stabilized values to determine if the person's performance is better or worse than the most recent previous session. If the person's performance was better than the previous session, then the algorithm(s) determine if the person's performance has reached a "normal" level of performance. If it has, then the algorithm(s) trigger moving on to a different VPT Session. If the person's performance has not yet reached a "normal" level, the algorithm(s) increase the session difficulty.

If on the other hand the person's performance has worsened or is the same since the last session, the algorithm(s) ascertain whether the person's performance has not improved for a series of sessions, or if this may just be a temporary occurrence. If the person's performance has not improved over the course of several sessions, the algorithm(s) are configured to move on to the next VPT Session. This is because some persons will need other aspects of their visual perception process improved before they will show improvement on particular VPT Sessions. The person can then come back to this VPT Session at another time. Otherwise, the algorithm(s) will decrease the difficulty of the VPTs and administer the same VPT Session.

Once these algorithm(s) have been run and the next VPT Session parameters are set and stored until the person requests another VPT Session. It should be noted that the new VPT Session parameters are generally not at the person's thresholds. Instead, the difficulty level of the new VPT Session is lowered in order to allow the person to ease into the new VPTs that are at his or her thresholds.

In one embodiment, an "n over 1" staircase method is employed when making changes to a parameter, (e.g. contrast level), of the VPT Images 100. What this means is that a person must correctly perform "n" VPTs before advancing to a more difficult VPT. The value of "n" preferably ranges from two to five. However, it only takes "m" incorrect responses to result in stepping back and decreasing the level of difficulty of the next VPT. Preferably, the value of "m" is one. This approach ensures that the person must truly make accurate perceptions in order to progress through the VPT Session. If the person is simply guessing and getting only 50% of the responses correct, statistically he or she will only step back and the VPTs will become easier because n>m. Using the "n over 1" staircase, a person cannot move forward in the VPT Session by randomly guessing.

When the person provides "n" correct responses, a parameter of the VPT Images 100 is changed to make the next VPT more difficult. So for a parameter, such as contrast, a new contrast parameter is calculated using the formula:

$$\text{Parameter}_{NEW\ CONTRAST\ LEVEL} = \text{Parameter}_{OLD\ CONTRAST\ LEVEL}/k$$

where the parameter contrast levels are defined in numerical terms and "k" is a coefficient to compensate for certain effects on a person's performance which are unrelated to the person's visual perception or acuity abilities.

Alternatively, when the person provides "m" incorrect responses, the next VPT is designed to be less difficult than the VPT that the person failed. Again using contrast level as the parameter to be changed, the new parameter for contrast level is calculated using the formula:

$$\text{Parameter}_{NEW\ CONTRAST\ LEVEL} = \text{Parameter}_{OLD\ CONTRAST\ LEVEL} * k$$

where, again, the parameter contrast levels are defined in numerical terms and "k" is a coefficient to compensate for certain effects on a person's performance which are unrelated to the person's visual perception or acuity abilities.

Notably, the value of the "k" coefficient for a particular person may be derived empirically, e.g., based on general population studies, but is preferably individually determined and calibrated on an ongoing basis for every person. It's purpose is to compensate for certain effects on a person's performance that are unrelated to the person's visual perception or acuity abilities, such as 1) Unusually high or low standard deviation. The gap between a person's best and worst performance may be quite large.
2) Weariness. A person's results are frequently much better at the beginning of a session then towards the end.
3) Suppression. Certain shapes on the screen may disturb a particular person's vision.
4) Facilitation. Providing a sound cue or some visual image on the screen may improve a person's performance.
5) Inconstancy. A person may make mistakes on very easy tasks that are unlikely for the particular person to fail, given his or her tested ability.

In some embodiments, a person may be assigned to a group of persons having similar performance characteristics and effects, and adopt a value for the "k" coefficient set for the entire group.

In another embodiment, when increasing or decreasing the difficulty of a VPT Session, the following weighted function is used to derive new parameters:

$$\text{Parameter}_{NEW\ VPT\ SESSION} = (\text{Parameter}_{NORMAL} - \text{Parameter}_{CURRENT}) * k$$

Notably, the parameter can be any of the ones mentioned herein, such as contrast level, or degree of offset.

In embodiments of the invention where several persons will be accessing one client terminal 820, such as at a clinic, client terminal 820 can download VPT Session parameters for a number of persons atone time. For instance, client terminal 820 may be in communication with host server 800 for a period of time, for example in the morning, to download VPT Session parameters for a number of persons. These persons can be persons who have scheduled appointments to access client terminal 820 during that day. This eliminates the need for constant or frequent on-line communications, and can also eliminate the need for individual usernames and passwords for persons as the entity running the client terminal can control who has access.

In this embodiment, the sets of person performance data generated during the numerous VPT Sessions administered to all of the persons can then be uploaded to host server 800 at one time. The data upload can take place anytime, for example during off peak hours, or even the next morning during the same period of time when new VPT Session parameters are being downloaded for that day's scheduled persons. It should be noted that the uploading and downloading of data may take place at any time of the day.

Notably, in various embodiments, the algorithm(s) may be different when working on different attributes abilities and even within a specific attribute, assuming a different state defined by the setup parameters—such as the combination of images size, display duration, orientation, gabor patch shape, etc.

In another embodiment, the VPT Images 100 are preformed and selected, rather than being generated dynamically. In such an embodiment, the VPT Session parameters comprise the specific VPT Images 100 themselves, rather than defining the images.

Selecting a VPT Session to Administer

Figure 10:
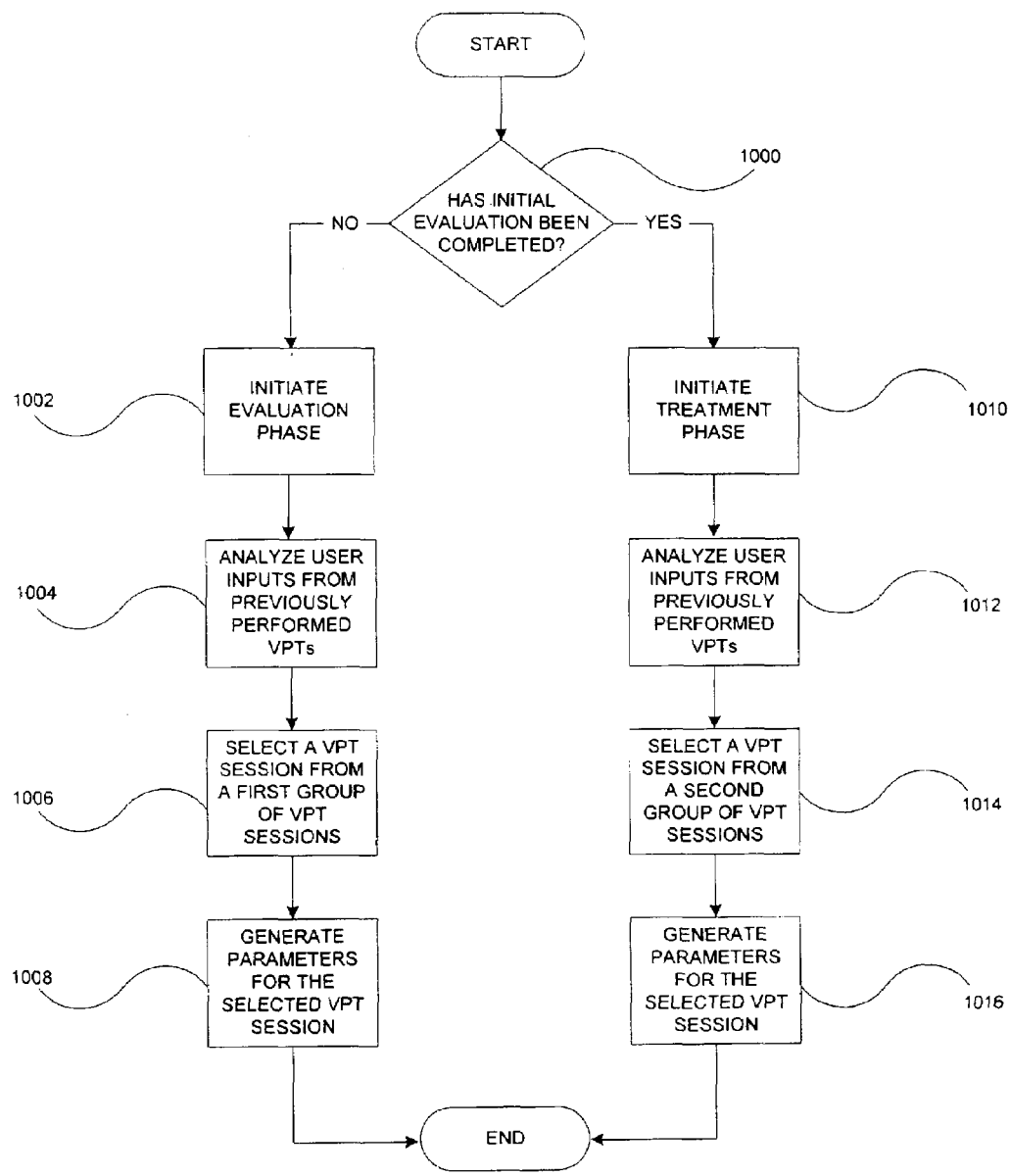

Turning to FIG. 10, a flowchart is illustrated that demonstrates how a VPT Session is selected. There are two forms of VPT Sessions available, an evaluation phase to ascertain a person's visual perception ability, and a treatment phase to improve the person's visual perception. Accordingly, as shown in step 1000, the first step in selecting a VPT Session is to determine whether the person has undergone the evaluation phase. If an evaluation has not been completed, the next step in the process is to move on to step 1002. Otherwise, the flowchart will continue at step 1010.

Starting with the evaluation phase and step 1002, a person undergoes the evaluation to enable ascertaining the condition of the person's visual perception process. This data allows generation of effective VPTs that target the person's visual perception deficiencies. It also allows for a baseline set of data to gauge whether the person's visual perception is improving over the course of a particular VPT Session and over time. The evaluation process can be performed as often as necessary or desired.

Moving to step 1004, user inputs and performance data from past VPT Sessions are analyzed. This data provides information that is useful for establishing parameters that select VPT Images 100 and VPT Sessions to use to evaluate the person's visual perception. For instance, if particular aspects of the person's visual perception have recently been evaluated, VPT Session is selected that evaluates a different aspect. Or if the user inputs from past VPT Sessions show that the person is deficient in a particular aspect of their visual perception, a VPT Session may be selected for further evaluating that particular aspect to determine whether there has been improvement or deterioration.

Moving to step 1006, a VPT Session is selected from a first group of potential VPT Sessions. VPTs within each VPT Session are used to collect data from the person regarding different aspects of the person's visual perception process to detect the existence of any physical or neural defects. VPTs are used to test for any one or all of the following:
- reduced visual acuity,
- abnormal contrast sensitivity functions,
- reduced vernier acuity,
- spatial distortion,
- abnormal spatial interactions,
- impaired contour detection,
- abnormally high degrees of intrinsic noise,
- as well as other aspects of the person's visual perception.

Moving to step 1008, once the VPT Session has been selected, parameters for the VPT Session are generated. These parameters define the VPT Images 100 and VPTs that are to be presented to the person, and in particular control the difficulty of the VPTs as well as other characteristics. Again, data from past VPT Sessions, including VPT Session parameters generated in accordance with step 916 of FIG. 9 above, can be used in setting these parameters.

Moving to step 1010, a treatment phase is initiated for improving various aspects of the visual perception process of a person and alleviate visual perception deficiencies. The flow of the treatment phase is almost identical to that of the evaluation phase.

Moving to step 1012, user inputs from past VPT Sessions are analyzed. Next, as shown in step 1014, a VPT Session is selected from a second group of VPT Sessions. This second group of VPT Sessions is different than the group described for the evaluation phase. Here, the second group of VPT Sessions comprises the following:
- a lateral masking treatment VPT Session,
- an acuity treatment VPT Session,
- an elongated stimuli treatment VPT Session,
- a stereoscopic treatment VPT Session,
- and other treatment VPT Sessions.

Moving to step 1016, as was the case for the evaluation phase, once a VPT Session has been selected, parameters are generated which, again, define the VPT Images 100 and VPTs that are to be presented to the person. Data from past VPT Sessions can be used in generating these parameters, including VPT Session parameters generated in accordance with step 916 of FIG. 9 above.

Client Terminal-Side Methods

Figure 11:
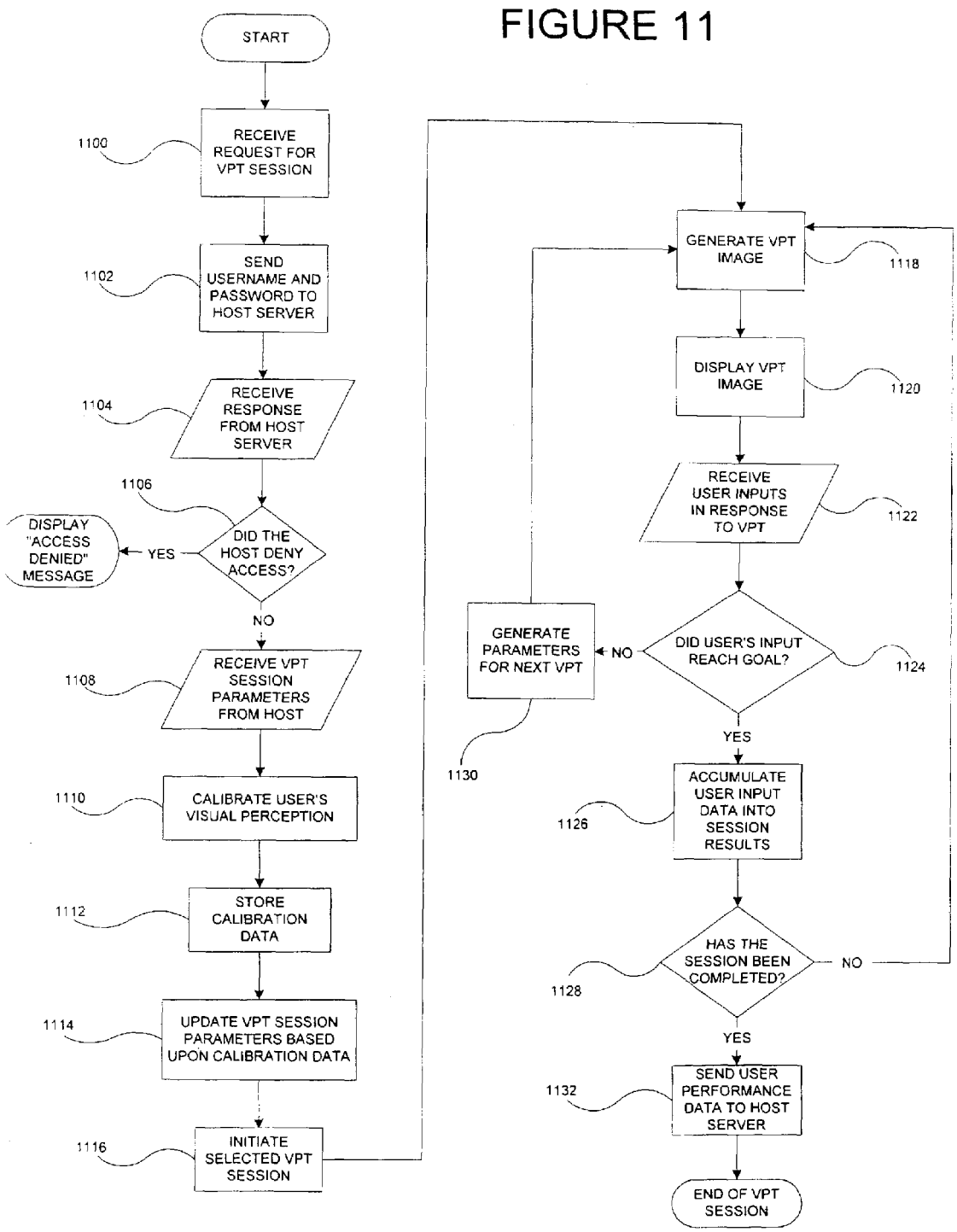
FIG. 11 is a flowchart depicting methods for identifying, quantifying and improving visual perception abilities of a person from the perspective of a client terminal in the system of FIG. 8.

FIG. 11 is a flowchart illustrating how preferred methods are carried out at client terminal 820. Starting with step 1100, client terminal 820 receives a request for a VPT Session from a person. For example, a person can arrive at client terminal 820 and enter a request for a VPT Session using an input device, such as a keyboard, at client terminal 820. The process of requesting a VPT Session generally comprises visiting a web site, such as a home page or authentication page provided by host server 800, and entering a username and password. The software that requests the username and password may be located on either host server 800 or client terminal 820.

Moving to step 1102, the VPT Session request and username/password information is sent from client terminal 820 to host server 800 over a communication network, such as the Internet 840. Again, the Internet will be used herein as the communication network. This transmission of data can be encrypted or use certificates to prevent others from accessing the username and password information.

In step 1104, client terminal 820 receives a response from host server 800 that either allows or denies access to a VPT Session. The response is transmitted over the Internet 840 and is sent after host server 800 has determined if the username and password supplied are authentic. As shown in step 1106, if the person is authentic and access is granted, the process continues at step 1108. Alternately, if host server 800 determines that the person is not authentic, access to a VPT Session is denied and the process ends with a message to the person indicating the denial of access.

Moving now to step 1108, VPT Session parameters for the current VPT Session are delivered to client terminal 820 from host server 800. These VPT Session parameters are used to define the VPTs, and VPT Images 100, that are presented to the person. The process of generating the VPT Session parameters was explained above with reference to steps 906 and 916 of FIG. 9, and steps 1008 and 1016 of FIG. 10.

Client terminal 820 has software residing on it configured to administer VPT Sessions to a person, and generally only requires VPT Session parameters from host server 800 to deliver the VPT Session. The software can be sent to client terminal 820 in any of a number of ways, including by Internet download, or via installation off of a magnetic or optical disk.

In step 1110, the person's visual perception is calibrated. The visual perception ability of a person can vary from day to day based on a variety of factors such as stress, energy level, fatigue, previous meals, time spent in front of a computer screen or television, and many others. Therefore, one or more tests of the person's visual perception are preferably run to see if their visual perception ability is diminished due to these types of factors.

Moving to steps 1112 and 1114, the collected calibration data is stored and the updated VPT Session parameters are downloaded during step 1108. The parameters are updated to compensate for any diminished visual perception ability detected during the calibration step 1110, thereby making the current VPT Session more effective and efficient. For instance, it the person's visual perception abilities have diminished by a certain amount, the VPT Session parameters can be lowered by that same amount to compensate for the diminished visual perception ability.

Moving to step 1116, the VPT Session is started. The VPT Session selected during the selection phase described in FIG. 10 is used.

In step 1118, one or more VPT Images 100 using the VPT Session parameters are generated. Again, the parameters provided by host server 800 may be used to generate the VPT Images 100 on the fly. In another embodiment, pre-formed VPT Images 100 may be used.

Moving to step 1120, after the one or more VPT Images 100 have been generated, they are used in a VPT which is presented to the person. The techniques used in VPTs were explained above.

After the VPT is presented, as shown in step 1122, an input from the person is received, which indicates whether or not the person correctly performed the VPT. As explained above, these inputs are used to gauge the person's visual perception ability and to analyze the person's performance over one or more VPT Sessions. The user inputs are also used to adjust the VPT Session parameters used in subsequent VPT Images 100.

Moving to step 1124, it is then determined whether the input demonstrates that the person has reached a predefined goal. This goal is set based on a variety of factors, including how the person has performed in previous VPT Sessions and during evaluation phases. An example of a goal can be to administer VPTs to the person until a desired level of improvement has been achieved, or until a certain number of incorrect responses has been received.

Moving to step 1130, if the goal has not been met, new VPT Images 100 are generated for use in a subsequent VPT, again based on the VPT Session parameters, which can be modified as the VPT Session is administered. The new VPT Images 100 are generally variations of the previous VPT Images 100, wherein parameters such as contrast, distance between objects, color, shape, size, or other parameters are changed. The new parameters can vary the difficulty level of the VPT that is displayed, generally based at least in part upon the person's inputs and performance over the preceding one or more VPTs. Once the new parameters are chosen, returning to step 1118, the next set of VPT Images 100 are displayed.

Moving to step 1126, after the goal has been reached, the inputs are accumulated into VPT Session results, and person performance data is generated. These results can later be analyzed to ascertain the condition of the person's visual perception process, and determine whether it is improving or regressing.

Moving to step 1128, it is then determined whether the entire VPT Session has been completed. If so, the person performance data, including the stabilized values and accumulated user inputs, are sent to host server 800 over the Internet 840 as shown in step 1132, and this particular VPT Session is ended. The person performance data can be sent to host server 800 in an encrypted format, or using certificates, to prevent unauthorized persons from viewing that individual's input data. If the VPT Session has not been completed, returning back to step 1118, new VPT Images 100 are generated to continue the current VPT Session.

Hardware Overview

Figure 12:
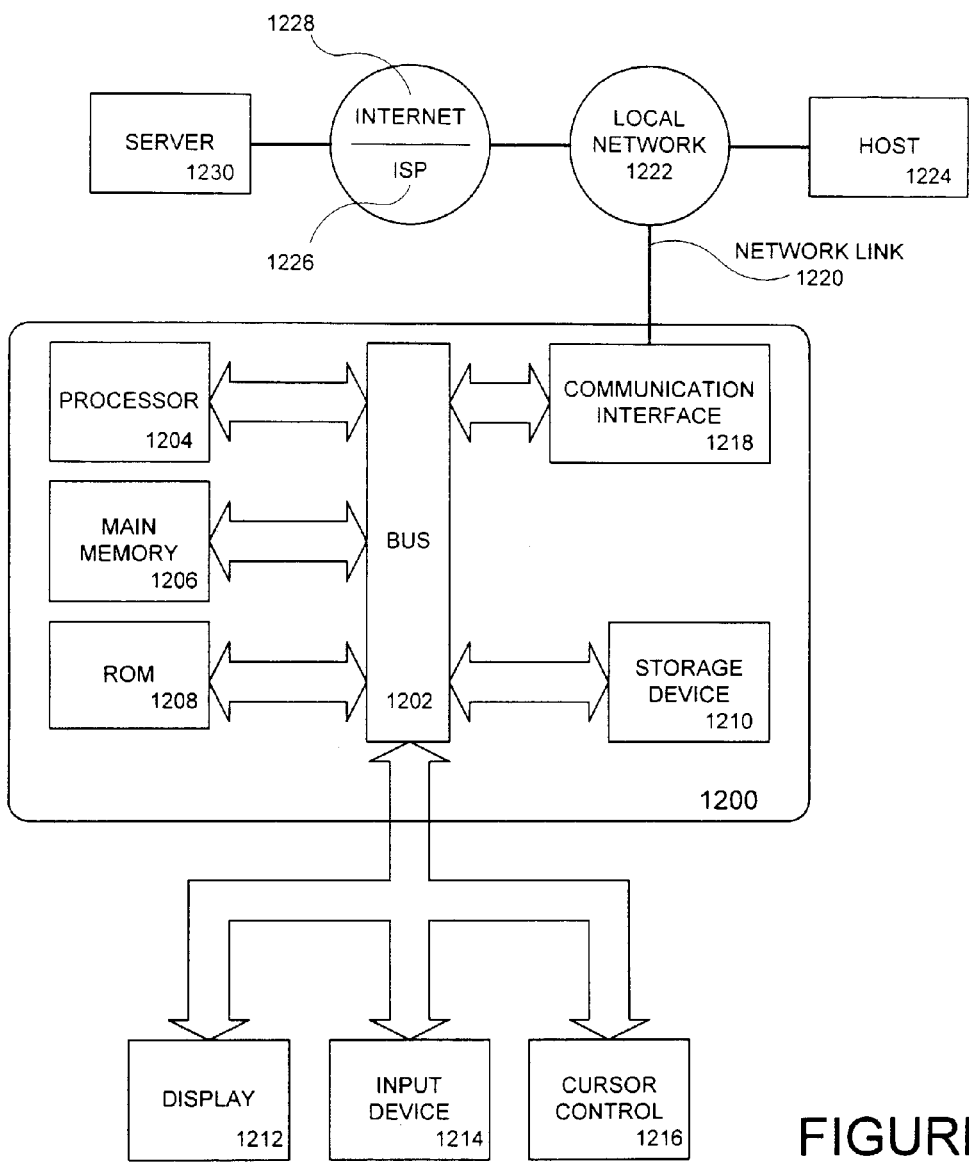
FIG. 12 illustrates an embodiment of a system configured to carry out methods for identifying, quantifying and improving visual perception abilities of a person, in accordance with the invention.

FIG. 12 is a block diagram of an exemplary computer system 1200 upon which preferred methods of the invention are implemented. The computer system of FIG. 12 can be used for host server 800, and/or for client terminal 820.

Computer system 1200 includes a bus 1202, or other communication mechanism for communicating information, and a processor 1204 coupled with bus 1202 for processing information. Computer system 1200 also includes a main memory 1206, such as a random access memory ("RAM"), or other dynamic (or "volatile") storage device, coupled to bus 1202. The main memory 1206 stores information and instructions executed by processor 1204 during execution. Main memory 1206 also stores temporary variables or other intermediate information during execution of instructions by processor 1206.

Computer system 1200 further includes a read only memory ("ROM") 1208 or other static (or "persistent") storage device (e.g., FLASH, PROM, EEPROM, etc.) coupled to bus 1202. The ROM 1208 stores static information and instructions for processor 1204. It is worth noting that one or more banks of memory can comprise ROM 1208. A storage device 1210, such as a magnetic disk or optical disk (or "hard disk", or "hard drive"), or another form of persistent storage device, is coupled to bus 1202. The storage device 1210 uses a computer readable medium to store information such as data structures and instructions, for example, accumulated user input data from completed VPT Sessions, processor executable instructions (i.e. software) configured to carry out the methods described above with reference to host server 800 and client terminal 820, and/or structures relating to the operating system or application programs that use the operating system.

Computer system 1200 is preferably coupled via bus 1202 to a display device 1212, such as a cathode ray tube ("CRT") or an active or passive-matrix display. The display 1212 presents images to an end-person, such as VPT Images 100. An input device 1214, including alphanumeric and other keys, is coupled to bus 1202. The input device 1214 communicates information and command selections to processor 1204. Another type of user input device is cursor control 1216, such as a mouse, trackball, or cursor direction keys, for communicating direction information and command selections to processor 1204 and for controlling cursor movement on display 1212. This input device 1214 typically has two degrees of freedom in two axes, a first axis (e.g., x) and a second axis (e.g., y), that allows the device to specify positions in a plane.

According to an aspect of the invention, the processor 1204 in the computer system 1200 executes one or more sequences of instructions (i.e. software 1205), contained in main memory 1206. Such instructions are read into main memory 1206 from another computer-readable medium, such as storage device 1210 or ROM 1208. The instructions can be executable object code or interpreted code that is processed by a run-time engine (e.g., Javascript).

Execution of the sequences of instructions contained in main memory 1206 causes processor 1204 to perform the methods of the invention as described herein, such as the methods described with reference to host server 800 and/or client terminal 820 above. In alternative embodiments, hard-wired circuitry can be used in place of or in combination with software instructions to implement the invention. Thus, embodiments of the invention are not limited to any specific combination of hardware circuitry and software.

The term "computer-readable medium" as used herein refers to any medium that participates in providing instructions to processor 1204 for execution. Such a medium can take many forms, including but not limited to, non-volatile media, volatile media, and transmission media. Non-volatile media includes, for example, optical or magnetic disks, such as storage device 1210. Volatile media includes dynamic memory, such as main memory 1206.

Transmission media includes coaxial cables, copper wire and fiber optics, including the wires that comprise bus 1202. Transmission media can also take the form of acoustic or light waves, such as those generated during radio-wave and infrared data communications.

Common forms of computer-readable media include, a floppy disk, a flexible disk, a hard disk, a magnetic tape, or any other magnetic media, a CD-ROM, any other optical media, punchcards, a paper-tape, any other physical media with patterns of holes, a RAM, a ROM, a FLASH, or any other memory chip or cartridge, a carrier wave as described hereinafter, or any other media from which a computer can read.

Various forms of computer-readable media can be involved in carrying one or more sequences of one or more instructions to processor 1204 for execution. For example, the instructions can initially be carried on a magnetic disk of a remote computer. The remote computer can load the instructions into its dynamic memory and send the instructions over a telephone line using a modem. A modem local to computer system 1200 can receive the data on the telephone line and use an infrared transmitter to convert the data to an infrared signal. An infrared detector coupled to bus 1202 can receive the data carried in the infrared signal and place the data on bus 1202. Bus 1202 carries the data to main memory 1206, from which processor 1204 retrieves and executes the instructions. The instructions received by main memory 1206 can optionally be stored on storage device 1210 before or after execution by processor 1204.

Computer system 1200 also includes a communication interface 1218 coupled to bus 1202. Communication interface 1218 provides a two-way data communication coupling to a network link 1220 that is connected to a local network 1222. For example, communication interface 1218 can be an integrated services digital network ("ISDN") card or a modem to provide a data communication connection to a corresponding type of telephone line. As another example, communication interface 1218 can be a local area network ("LAN") card to provide a data communication connection to a compatible LAN. Wireless links can also be implemented. In any such implementation, communication interface 1218 sends and receives electrical, electromagnetic or optical signals that carry digital data streams representing various types of information.

Network link 1220 preferable provides data communication through one or more networks to other data devices. For example, network link 1220 can provide a connection through local network 1222 to a host computer 1224 or to data equipment operated by an Internet Service Provider ("ISP") 1226. ISP 1226 in turn provides data communication services through the Internet 1228. Local network 1222 and Internet 1228 both use electrical, electromagnetic or optical signals that carry digital data streams. The signals through the various networks and the signals on network link 1220 and through communication interface 1218, which carry the digital data to and from computer system 1200, are exemplary forms of carrier waves transporting the information.

Computer system 1200 can send messages and receive data, including program code, through the network(s), network link 1220 and communication interface 1218. In the Internet example, a server 1230 might transmit requested code for an application program through Internet 1228, ISP 1226, local network 1222 and communication interface 1218—for example using the FTP protocol. In accordance with the invention, one such downloaded application is executable software code or computer configuration parameters that perform the methods of the invention.

The received code can be executed by processor 1204 as it is received, and/or stored in main memory 1206, storage device 1210, or other non-volatile storage for later execution. In this manner, computer system 1200 can obtain application code in the form of a carrier wave.

Thus, methods and systems for analyzing and improving the visual perception process of a person have been disclosed. It should be noted that the disclosed methods and systems are useful for improving the visual perception of any person, no matter whether the person has normal or abnormal visual perception. The invention can also be used to diagnose and improve the vision of observers suffering from problems such as amblyopia, myopia, hyperopia, presbyopia, super-normal vision, or dyslexia. Even persons with anatomical or functional problems, such as macular degeneration, can improve what vision they have with the methods and apparatus of the invention. In addition to treating visual perception, the methods and systems of the invention can also be used in diagnosing major depression.

While various embodiments of the invention have been shown and described, it will be apparent to those skilled in the art that numerous alterations may be made without departing from the inventive concepts presented herein. Thus, the invention is not to be limited except in accordance with the following claims and their equivalents.

The invention claimed is:

1. A system for identifying deficiencies, inefficiencies, or both, in neuronal interactions of a person's visual cortex, the system comprising: a) a processor; b) an image generator coupled to the processor, c) the processor and image generator configured to generate visual stimuli comprising arrangements of one or more target images each flanked by one or more flanking images of similar configuration as the respective target image, each arrangement designed to induce a level of neuronal facilitation and suppression in a person's visual cortex, the arrangements comprising a parameter of the one or more target images and the respective flanking images; and d) an input device coupled to the processor, the input device configured to receive the person's responses to the visual stimuli, the responses indicating detection or discrimination by the person of the one or more target images of the respective arrangements; e) the processor and image generator configured to generate at least some of the visual stimuli based at least in part upon the person's responses to previous visual stimuli, the at least some visual stimuli designed to induce differing levels of facilitation and suppression in the person's visual cortex; f) the processor and image generator being configured to generate sufficient visual stimuli of differing levels of facilitation and suppression in the person's visual cortex until responses to a sufficient number of facilitation and suppression levels are received from the person such that deficiencies, inefficiencies, or both, in neuronal interactions of the person's visual cortex may be identified by comparing a function of the person's responses to a normative response function of persons without known vision deficiencies.

2. The system of claim 1, the visual stimuli arrangements comprising a parameter of global orientation of the one or more target images and the respective flanking images.

3. The system of claim 1, the visual stimuli arrangements comprising a parameter of local orientation of the one or more target images and the respective flanking images.

4. The system of claim 1, the visual stimuli arrangements comprising a parameter of the number of the one or more target images and the respective flanking images.

5. The system of claim 1, the visual stimuli arrangements comprising a parameter of contrast of the one or more target images and the respective flanking images.

6. The system of claim 1, the visual stimuli arrangements comprising a parameter of spatial frequency of the one or more target images and the respective flanking images.

7. The system of claim 1, the visual stimuli arrangements comprising a parameter of duration time of the one or more target images and the respective flanking images.

8. The system of claim 1, the visual stimuli arrangements comprising a parameter size of the one or more target images and the respective flanking images.

9. The system of claim 1, the processor configured to provide to the person one or more treatment sessions for improving identified deficiencies, inefficiencies, or both, in said neuronal functions of the person's visual cortex, the one or more treatment sessions including the processor and image generator generating visual stimuli arrangements, each arrangement comprising one or more target images each flanked by one or more flanking images of similar configuration as the respective target image designed to modify levels of neuronal facilitation and/or suppression in the person's visual cortex;

the input device receiving responses from the person indicating detection or discrimination of the target images in the respective visual stimuli arrangements; and the processor comparing the person's responses with prior responses received from the person to the same or similar visual stimuli arrangements weighted with selected normative responses to such visual stimuli arrangements, wherein at least some of the visual stimuli arrangements are based at least partly on results of a preceding comparison, until a sufficient number of responses are received from the person so that improvement in deficiencies, inefficiencies, or both, in neuronal interactions of the person's visual cortex may be identified by comparing a function of the person's responses to a normative response function of persons without known vision deficiencies.

10. The system of claim 9, the processor further configured to measure a level of neuronal performance in the person's visual cortex.

11. The system of claim 10, the processor further configured to identify a level of neuronal performance in the person's visual cortex at which further improvement in the neuronal performance is unlikely.

12. A method for identifying deficiencies, inefficiencies, or both, in neuronal interactions of a person's visual cortex, the method comprising:

(a) providing to the person visual stimuli comprising an arrangement of one or more target images each flanked by one or more flanking images of similar configuration as the respective target image, the arrangement designed to induce a level of neuronal facilitation and suppression in the person's visual cortex; the arrangement comprising a parameter of the one or more target images and the respective flanking images;

(b) receiving from the person a response to the visual stimuli provided in step (a), the response indicating detection or discrimination by the person of the one or more target images; and (c) providing further visual stimuli to the person based at least in part on the response received in step (b), the further visual stimuli comprising a further arrangement of one or more target images each flanked by a pair of flanking images of similar configuration as the respective target image and designed to induce a different level of facilitation and suppression in the person's visual cortex than the visual stimuli provided in step (a); said steps (a)–(c) being repeated until responses to a sufficient number of facilitation and suppression levels are received from the person such that deficiencies, inefficiencies, or both, in neuronal interactions of the person's visual cortex may be identified by comparing a function of the person's responses to a normative response function of persons without known vision deficiencies.

13. The method of claim 12, the visual stimuli arrangements comprising a parameter of global orientation of the one or more target images and the respective flanking images.

14. The method of claim 12, the visual stimuli arrangements comprising parameter of local orientation of the respective target images and the one or more flanking images.

15. The method of claim 12, the visual stimuli arrangements comprising a parameter of the number of the one or more target images and the respective flanking images.

16. The method of claim 12, the visual stimuli arrangements comprising a parameter of contrast of the one or more target images and the respective flanking images.

17. The method of claim 12, the visual stimuli arrangements comprising a parameter of spatial frequency of the one or more target images and the respective flanking images.

18. The method of claim 12, the visual stimuli arrangements comprising a parameter of duration time of the one or more target images and the respective flanking images.

19. The method of claim 12, the visual stimuli arrangements comprising a parameter of size of the one or more target images and the respective flanking images.

20. The method of claim 12, further comprising providing to the person one or more treatment sessions for improving identified deficiencies, inefficiencies, or both, in said neuronal functions of the person's visual cortex, the one or more treatment sessions including:

(d) providing to the person a plurality of visual stimuli arrangements, each arrangement comprising one or more target images each flanked by a pair of flanking images designed to modify levels of neuronal facilitation and/or suppression in the person's visual cortex;

(e) receiving responses from the person indicating detection or discrimination of the target images in the respective visual stimuli arrangements;

(f) comparing the person's responses with prior response received from the person to the same or similar visual stimuli arrangements; and (g) repeating steps (d)–(f), the visual stimuli arrangements provided in each step (d) based at least partly on results of the preceding comparison step (f), until a sufficient number of responses are received from the person so that improvement in deficiencies, inefficiencies, or both, in neuronal interactions of the person's visual cortex may be identified by comparing a function of the person's responses to a normative response function of persons without known vision deficiencies.

21. The method of claim 20, further comprising measuring a level of neuronal performance in the person's visual cortex.

22. The method of claim 21, further comprising identifying a level of neuronal performance in the person's visual cortex at which further improvement in the neuronal performance is unlikely.

* * * * *